United States Patent
Chopade et al.

(10) Patent No.: US 7,341,868 B2
(45) Date of Patent: Mar. 11, 2008

(54) PLASMID ENCODING IAA AND A METHOD THEREOF

(75) Inventors: Balu Ananda Chopade, Pune (IN); Shilpa Bhagavant Huddedar, Pune (IN); Ashvini Mohnish Shete, Pune (IN); Jayant Narayan Tilekar, Pune (IN); Dilip Dattatray Dhavale, Pune (IN); Sharad Damodar Gore, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 283 days.

(21) Appl. No.: 10/834,698

(22) Filed: Apr. 28, 2004

(65) Prior Publication Data

US 2005/0070435 A1    Mar. 31, 2005

Related U.S. Application Data

(66) Substitute for application No. 60/466,330, filed on Apr. 29, 2003.

(51) Int. Cl.
*C12N 15/63* (2006.01)
*C12N 1/20* (2006.01)
*C12Q 1/68* (2006.01)
*A01H 5/00* (2006.01)

(52) U.S. Cl. .............................. 435/320.1; 435/252.1; 435/6

(58) Field of Classification Search ..................... None
See application file for complete search history.

(56) References Cited

OTHER PUBLICATIONS

Huddedar et al. Isolation, Characterization, and Plasmid pUPI126-Mediated Indole-3-Acetic Acid Production in Acinetobacter Srains from Rhizosphere of Wheat. Appl. Biochem. Biotechnol., Jul.-Dec. 2002;102-103(1-6):21-39.*

* cited by examiner

*Primary Examiner*—David Guzo
*Assistant Examiner*—Michele K. Joike
(74) *Attorney, Agent, or Firm*—Drinker, Biddle & Reath LLP.

(57) ABSTRACT

The present invention relates to a plasmid pUPI126 encoding indole-3 acetic acid (IAA) production, *Acinetobacter* strains having plasmid pUPI126, a bioinoculum for promoting growth of wheat plant, and a method of promoting wheat plant growth, the method comprising treating wheat seeds with the bioinoculum.

11 Claims, 6 Drawing Sheets

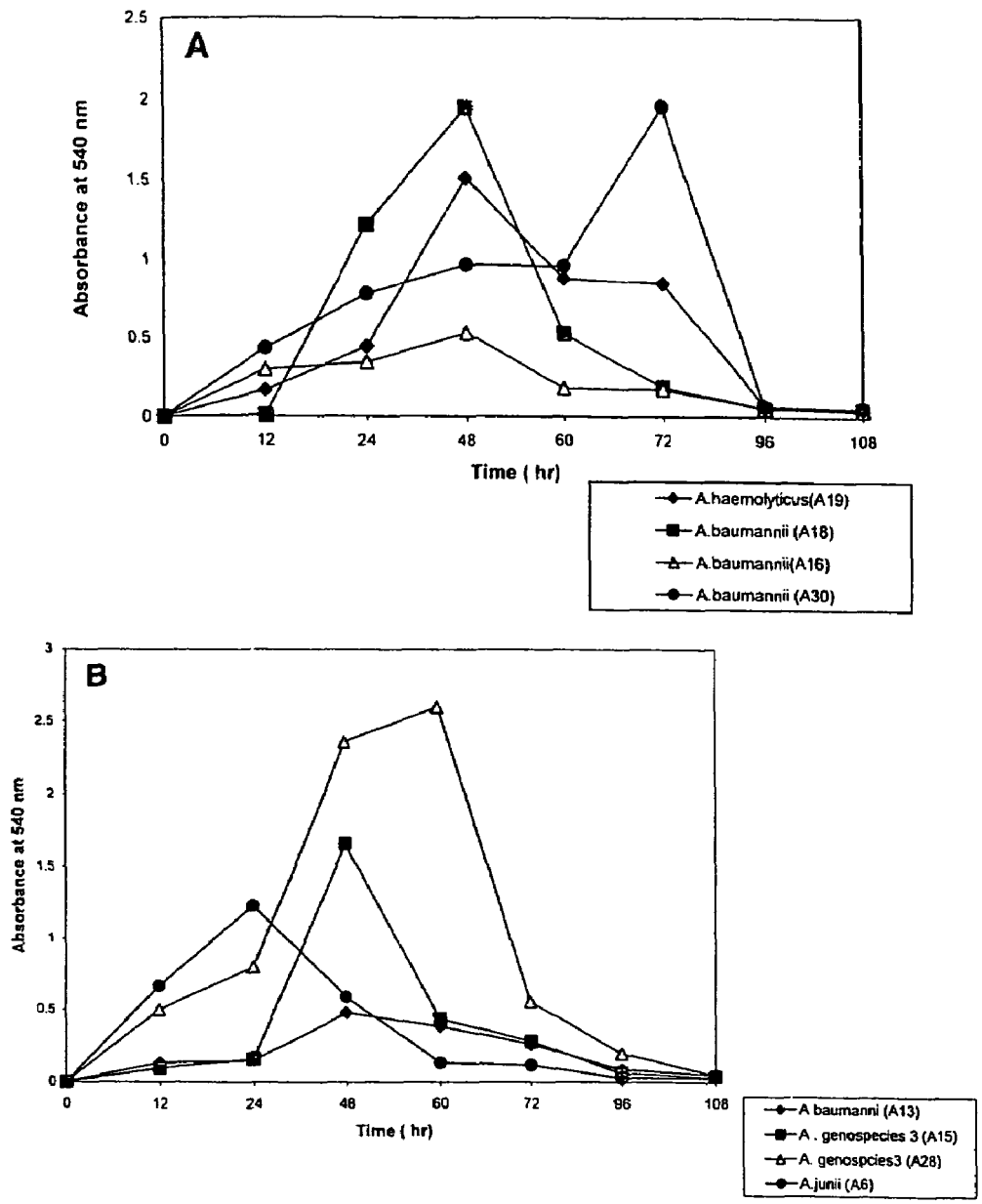
Fig. 1. (A) IAA production by four *Acinetobacter* genospecies—*A. haemolyticus* (A19) and *A. baumannii* (A18, A16, and A30)—isolated from rhizosphere of wheat; (B) IAA production of four *Acinetobacter* genospecies—*A. baumannii* (A13), *A. genospecies 3* (A15 and A28), and *A. junii* (A6)—isolated from rhizosphere of wheat.

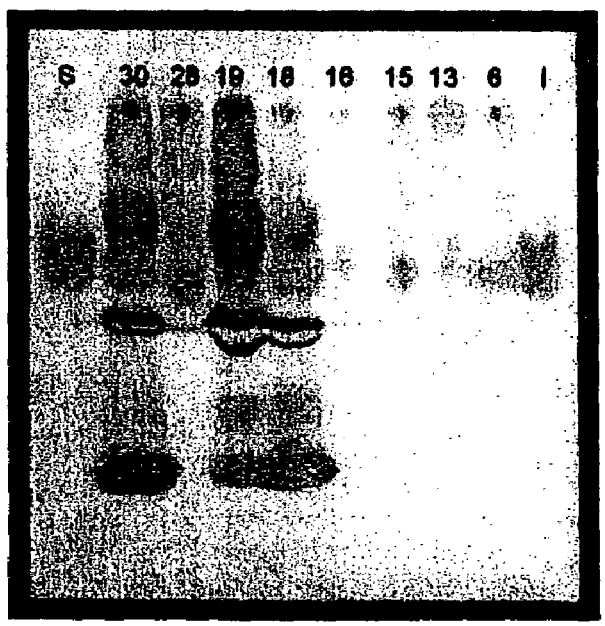
Fig. 2. TLC of purified IAA produced from *Acinetobacter* genospecies. S, purified IAA; 30, *A. baumannii* (A30); 28, *A. genospecies* 3 (A28); 19, *A. haemolyticus* (A19); 18, *A. baumannii* (A18); 16, *A. baumannii* (A16); 15, *Acinetobacter* genospecies 3 (A15); 13, *A. baumannii* (A13); 6, *A. junii* (A6); I, standard IAA.

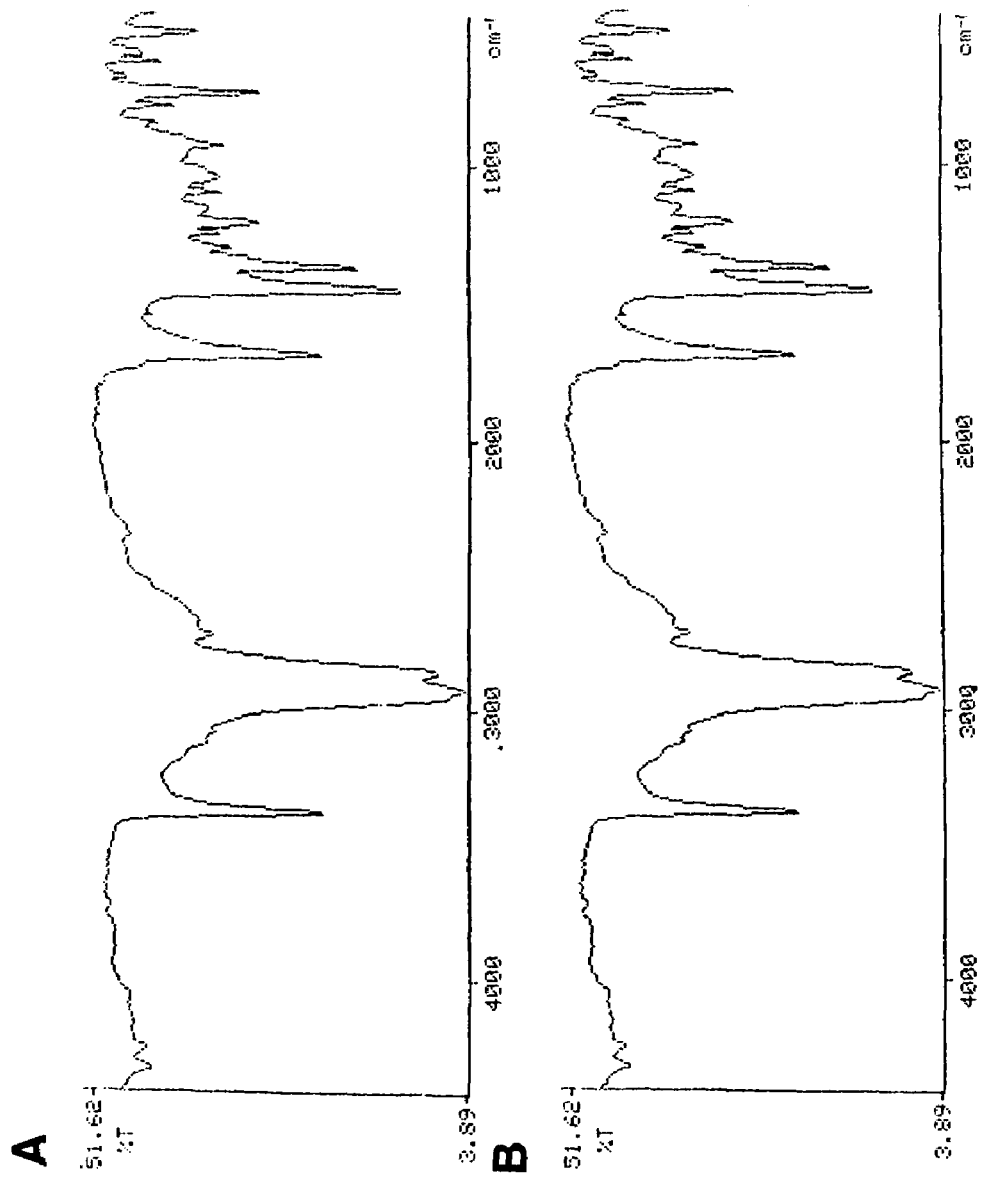
Fig. 3. (A) IR spectrum of purified IAA *Acinetobacter* genospecies. (B) IR spectrum of standard IAA from Sigma. %T, percentage of transmission; cm$^{-1}$, wavelength in centimeters.

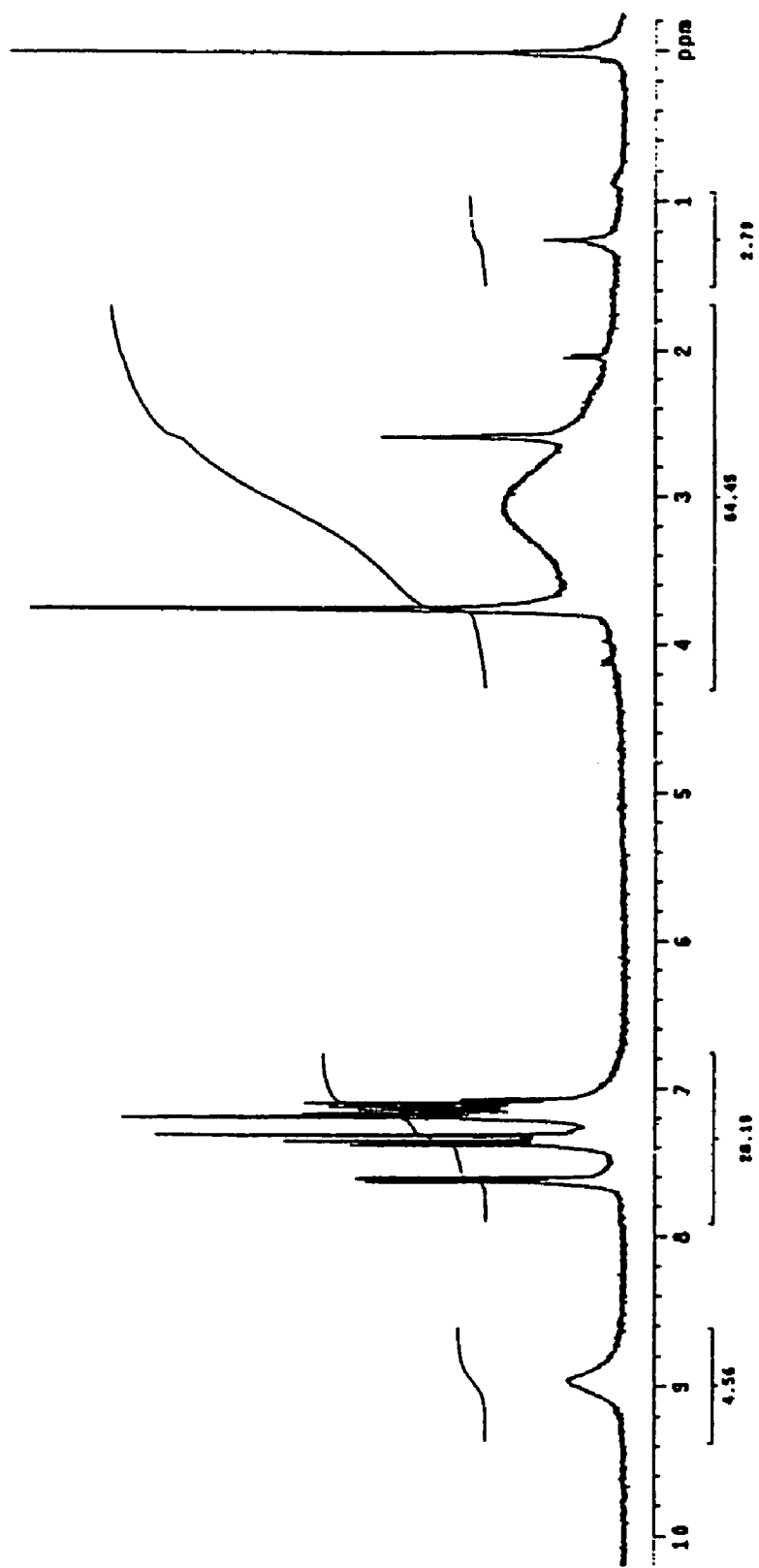
Fig. 4. ¹H-NMR analysis of purified IAA from *Acinetobacter* genospecies.

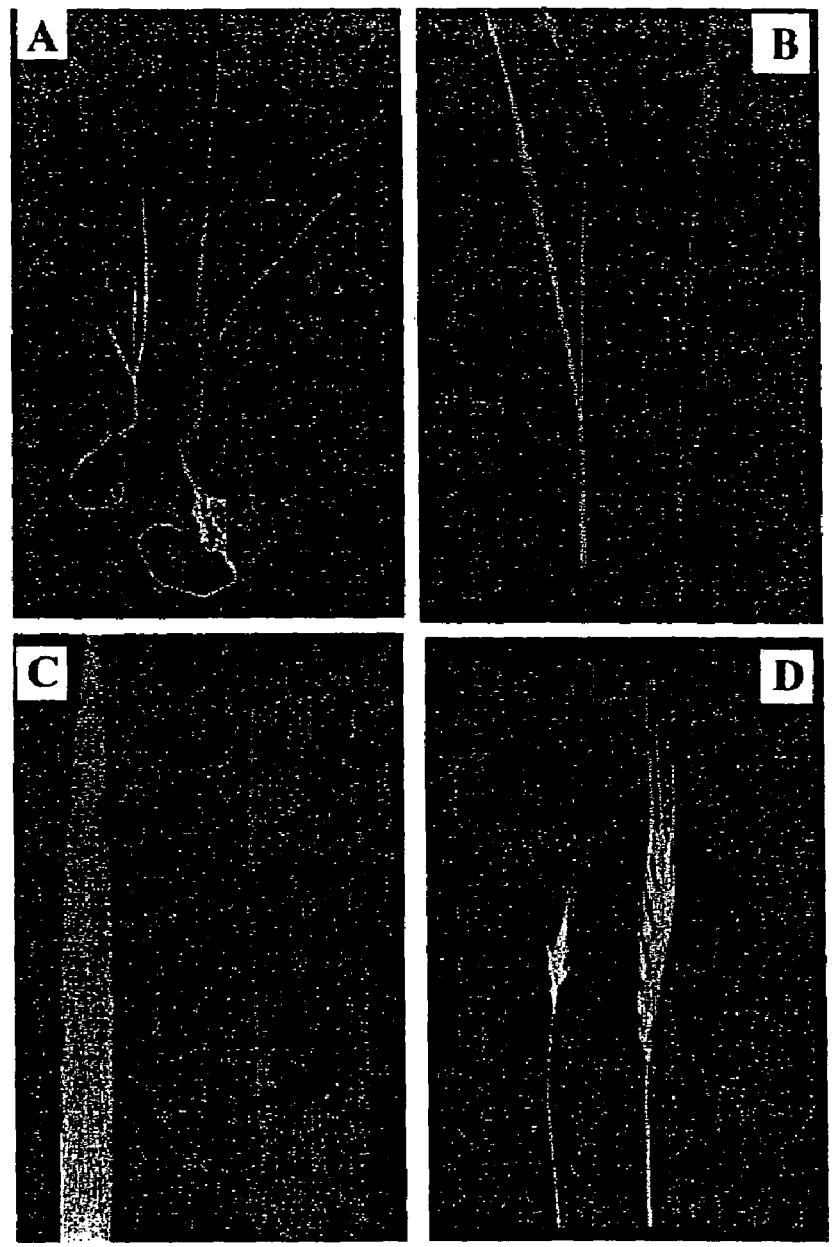
Fig. 5. Effect of IAA produced by *Acinetobacter* genospecies on growth of wheat plant:
(A) Root and shoot length of 21-d wheat plant; (B) shoot width of 60-d wheat plant; (C) leaf width of 60-d wheat plant; (D) fruiting size and number of grains of 75-d wheat plant.

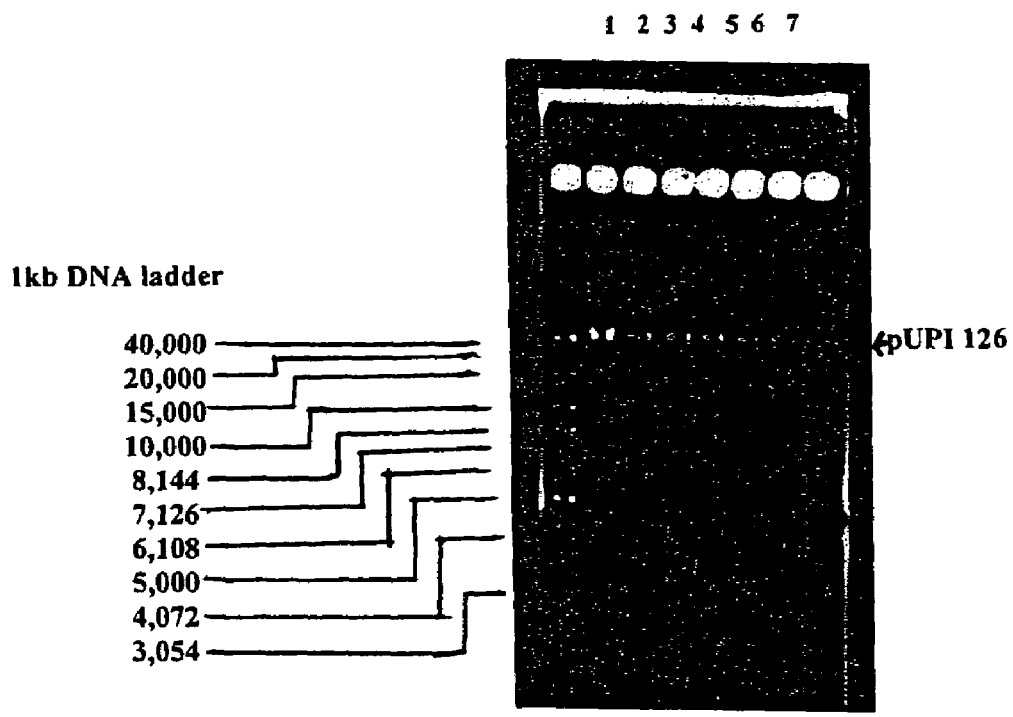
Fig. 6. Plasmid pUPI126 in IAA-producing *Acinetobacter* genospecies. Lane 1, *A. hemolyticus* (A19); lane 2, *A. baumannii* (A13); lane 3, *A. baumannii* (A16); lane 4, *A. genospecies 3* (A15); lane 5, *A. baumannii* (A18); lane 6, *A. juni* (A6); lane 7, *A. genospecies 3* (A28).

PLASMID ENCODING IAA AND A METHOD THEREOF

FIELD OF THE INVENTION

The present invention relates to a plasmid pUPI126, encoding indole-3 acetic acid (IAA) production; it also relates to *Acinetobacter* strains having plasmid pUPI126; a bioinoculum for promoting growth of wheat plant, and lastly, it relates to a method of promoting wheat plant growth, said method comprising treating wheat seeds with the bioinoculum.

BACKGROUND OF THE INVENTION

*Acinetobacter* species are ubiquitous in nature (Baumann, 1968; Juni, 1972). *Acinetobacter* is commonly found in soil, water, food and also on healthy human skin. (Saha & Chopade, 2001; Patil & Chopade 2001; Dhakephalkar et al, 1994a). *Acinetobacter* is one of the known opportunistic human pathogens (Dhakephalkar & Chopade 1994a; Chopade et al, 1994a & 1994b). It also possesses a number of naturally occurring plasmids exhibiting resistance to antibiotics and heavy metals (Deshpande et al 1994; Shakibaie et al, 1999). There are few reports on the presence of *Acinetobacter* in soil; however, detailed studies regarding its occurrence, distribution, growth pattern, physiology and interactions with other soil microorganisms are not known. There is only one statement on the presence of *Acinetobacter* in wheat rhizosphere (Kleeberger et al, 1983). However, detailed information about the role of *Acinetobacter* in rhizosphere is not known.

Soil is a rich environment for growth of microorganisms, and specifically rhizosphere is a highly specialized environment in soil for growth of microorganisms. Since rhizosphere contains a large number of microorganisms one would expect plasmid transfer and dynamics of plasmid transfer from *Acinetobacter* to other microorganisms and vice versa in the rhizosphere environment. The rhizosphere of each and every plant is very specific with respect to the root exudates, as they are the main source of nutrients for rhizosphere microorganisms (Subba Rao, 1986).

Until now there has been no report on the involvement of plasmids in the production of IAA from the genus *Acinetobacter*. IAA is one of the major plant growth promoting hormones produced by plants as well as some bacteria and fungi. (Arshad & Frankenberger, 1991). Many species of bacteria produce IAA, especially when growth media are supplemented with tryptophan, a precursor of IAA. A number of microorganisms like *Agrobacterium tumefaciens, Agrobacterium rhizogenes, Pseudomonas savastanoi, Pseudomonas* spp., (Leinhos & Vocek, 1984), *Rhizobium* spp, (Baldi et al, 1991), *Bradyrhizobium* spp. and *Azospirillum* spp (Bashan et al, 1989) present in the rhizosphere of plants are known to produce IAA (Costacurta & Vanderleyden, 1995). To some extent, the biosynthesis of plant growth promoting substances such as auxins from phosphate solubilizing rhizobacteria from rhizosphere of wheat and rye has been reported (Leinhos & Vocek, 1984).

The aim of the present work was to isolate and characterize *Acinetobacter* from rhizosphere of wheat and to find out the role of *Acinetobacter* in plant growth promotion in general and involvement of plasmids in the production of plant growth promoting substance such as indole acetic acid (IAA).

Acinetobacters were isolated from rhizosphere of wheat. The variety of wheat plant was HD 2189 ICAR, New Delhi, India. The rhizosphere soil was collected throughout the December to March 1998 growing season, at different stages of the life cycle of the wheat plant: control soil (0 d), elongation (30 d) flowering stage (45 d), fruiting stage (60 d) and ripened fruiting stage (75 d). The rhizosphere was collected from three areas—rhizosphere soil (RS), rhizoplane (RP), and non rhizosphere soil (NRS). The samples were collected from an agricultural field of Mahatma Phule Agriculture College, Shivajinagar, Pune, Maharashtra, India. Samples were brought to a laboratory and processed immediately within half an hour.

OBJECTS OF THE INVENTION

The main object of the present invention is to develop a plasmid encoding indole-3 acetic acid (IAA) production.

Another main object of the present invention relates to *Acinetobacter* strains encoding indole-3 acetic acid (IAA) production.

Yet another object of the present invention relates to developing a bioinoculum for promoting growth of wheat plants.

Still another object of the present invention relates to a method of promoting wheat plant growth.

SUMMARY OF THE INVENTION

The present invention relates to a plasmid pUPI126 encoding indole-3 acetic acid (IAA) production. The invention also relates to *Acinetobacter* strains having plasmid pUPI126, a bioinoculum for promoting growth of wheat plants, and a method of promoting wheat plant growth, the method comprising treating wheat seeds with the bioinoculum.

DESCRIPTION OF THE INVENTION

Accordingly, the present invention relates to a plasmid pUPI126 encoding indole-3 acetic acid (IAA) production. The invention also relates to a *Acinetobacter* strains having plasmid pUPI126, a bioinoculum for promoting growth of wheat plants, and a method of promoting wheat plant growth, said method comprising treating wheat seeds with the bioinoculum.

In yet another embodiment of the present invention, a plasmid pUPI126 encodes indole-3 acetic acid (IAA) production.

In still another embodiment of the present invention, the plasmid is of 40 Kb size.

In yet another embodiment of the present invention, the plasmid encodes resistance to selenium, tellurium, and lead.

In another embodiment of the present invention, *Acinetobacter* strains having plasmid pUPI126 encode indole-3 acetic acid (IAA) production.

In still another embodiment of the present invention, the *Acinetobacter* strains are selected from the group comprising *Acinetobacter haemolyticus* A19, *Acinetobacter* genospecies A28, *Acinetobacter* genospecies A15, *Acinetobacter baumannii* A13, *Acinetobacter baumannii* A16, *Acinetobacter baumannii* A18, *Acinetobacter baumannii* A30, and *Acinetobacter junii* A6.

In yet another embodiment of the present invention, the plasmid encodes resistance to selenium, tellurium, and lead.

In still another embodiment of the present invention, the strain *Acinetobacter haemolyticus* A19 is characterized as:

| Characteristics | *A. haemolytivus* A19 |
|---|---|
| Growth at: | |
| 44° C. | ++ |
| 41° C. | ++ |
| 37° C. | ++ |
| 28° C. | ++ |
| Pigment production | Yellow |
| Acid from Glucose | ++ |
| Gelatin Hydrolysis | ++ |
| Haemolysis | ++ |
| Citrate (Simmons) | ++ |
| Utilization of: | |
| DL-Lactate | ++ |
| L-Phenylalanine | ++ |
| Phenyl acetate | ++ |
| Malonate | ++ |
| L-Histidine | ++ |
| D-Malate | ++ |
| L-Aspartate | -- |
| L-Leucine | -- |
| L-Tyrosine | ++ |
| β-Alanine | ++ |
| L-Glycine | ++ |
| Trans-Aconitate | -- |
| D-Glucose | ++ |
| L-Tryptophane | ++ |
| Na-Acetate | ++ |
| Oxalate | ++ |
| Ethanol | ++ |
| L-Arginine | ++ |
| L-Ornithine | ++ |
| DL 4-Aminobutyrate | ++ |
| Tween 20 | ++ |
| Tween 80 | ++ |
| Other tests: | |
| Indole | -- |
| MR | -- |
| VP | -- |
| Triple sugar iron test | ++ |

In another embodiment of the present invention, the strain *Acinetobacter genospecies* A28 is characterized as:

| Characteristics | *A. genospecies* 3 A28 |
|---|---|
| Growth at: | |
| 44° C. | -- |
| 41° C. | ++ |
| 37° C. | ++ |
| 28° C. | ++ |
| Pigment production | Pink |
| Acid from Glucose | ++ |
| Gelatin Hydrolysis | -- |
| Haemolysis | -- |
| Citrate (Simmons) | ++ |
| Utilization of: | |
| DL-Lactate | ++ |
| L-Phenylalanine | ++ |
| Phenyl acetate | -- |
| Malonate | ++ |
| L-Histidine | ++ |
| D-Malate | ++ |
| L-Aspartate | ++ |
| L-Leucine | ++ |
| L-Tyrosine | ++ |
| β-Alanine | ++ |
| L-Glycine | ++ |
| Trans-Aconitate | ++ |
| D-Glucose | ++ |
| L-Tryptophane | ++ |
| Na-Acetate | ++ |
| Ethanol | ++ |
| L-Arginine | ++ |
| L-Ornithine | ++ |
| DL 4-Aminobutyrate | ++ |
| Other tests: | |
| MR | ++ |
| VP | -- |
| Triple sugar ion test | ++ |

In another embodiment of the present invention, the strain *Acinetobacter* genospecies a15 is characterized as:

| Characteristics | *A. genospecies* A15 |
|---|---|
| Growth at: | |
| 44° C. | -- |
| 41° C. | ++ |
| 37° C. | ++ |
| 28° C. | ++ |
| Pigment production | Pink |
| Acid from Glucose | ++ |
| Gelatin Hydrolysis | -- |
| Haemolysis | -- |
| Citrate (Simmons) | ++ |
| Utilization of: | |
| DL-Lactate | ++ |
| L-Phenylalanine | ++ |
| Phenyl acetate | ++ |
| Malonate | ++ |
| L-Histidine | ++ |
| D-Malate | ++ |
| L-Aspartate | ++ |
| L-Leucine | ++ |
| L-Tyrosine | ++ |
| β-Alanine | ++ |
| L-Glycine | ++ |
| Trans-Aconitate | ++ |
| D-Glucose | ++ |
| L-Tryptophane | ++ |
| Na-Acetate | ++ |
| Ethanol | ++ |
| L-Arginine | ++ |
| L-Ornithine | ++ |
| DL 4-Aminobutyrate | ++ |
| Other tests: | |
| MR | ++ |
| VP | -- |
| Triple sugar ion test | ++ |

In another embodiment of the present invention, the strain *Acinetobacter baumannii* A13 is characterized as:

| Character | *A. baumannii* A13 |
|---|---|
| Growth at: | |
| 44° C. | ++ |
| 41° C. | ++ |
| 37° C. | ++ |
| 28° C. | ++ |
| Pigment production | NP |
| Acid from Glucose | ++ |
| Gelatin Hydrolysis | -- |

| Character | A. baumannii A13 |
|---|---|
| Haemolysis | ++ |
| Citrate (Simmons) | ++ |
| Utilization of: | |
| DL-Lactate | ++ |
| L-Phenylalanine | ++ |
| Phenyl acetate | ++ |
| Malonate | ++ |
| L-Histidine | ++ |
| D-Malate | ++ |
| L-Aspartate | ++ |
| L-Leucine | ++ |
| L-Tyrosine | ++ |
| β-Alanine | ++ |
| L-Glycine | ++ |
| Trans-Aconitate | -- |
| D-Glucose | ++ |
| L-Tryptophane | ++ |
| Na-Acetate | ++ |
| Ethanol | ++ |
| L-Arginine | ++ |
| L-Ornithine | ++ |
| DL 4-aminobutyrate | ++ |
| Other tests: | |
| Indole | -- |
| MR | -- |
| Triple sugar iron test | ++ |

In another embodiment of the present invention, the strain *Acinetobacter baumannii* A16 is characterized as:

| Character | A. baumannii A16 |
|---|---|
| Growth at: | |
| 44° C. | ++ |
| 41° C. | ++ |
| 37° C. | ++ |
| 28° C. | ++ |
| Pigment production | Brown |
| Acid from Glucose | NP |
| Gelatin Hydrolysis | -- |
| Haemolysis | -- |
| Citrate (Simmons) | ++ |
| Utilization of: | |
| DL-Lactate | ++ |
| L-Phenylalanine | ++ |
| Phenyl acetate | -- |
| Malonate | ++ |
| L-Histidine | ++ |
| D-Malate | ++ |
| L-Aspartate | ++ |
| L-Leucine | ++ |
| L-Tyrosine | ++ |
| β-Alanine | ++ |
| L-Glycine | ++ |
| Trans-Aconitate | ++ |
| D-Glucose | ++ |
| L-Tryptophane | ++ |
| Na-Acetate | ++ |
| Ethanol | ++ |
| L-Arginine | ++ |
| L-Ornithine | ++ |
| DL 4-aminobutyrate | ++ |
| Other tests: | |
| Indole | -- |
| MR | -- |
| Triple sugar iron test | ++ |

In yet another embodiment of the present invention, the strain *Acinetobacter baumannii* A 18 is characterized as:

| Character | A. baumannii A18 |
|---|---|
| Growth at: | |
| 44° C. | ++ |
| 41° C. | ++ |
| 37° C. | ++ |
| 28° C. | ++ |
| Pigment production | Yellow |
| Acid from Glucose | ++ |
| Gelatin Hydrolysis | -- |
| Haemolysis | -- |
| Citrate (Simmons) | ++ |
| Utilization of: | |
| DL-Lactate | ++ |
| L-Phenylalanine | ++ |
| Phenyl acetate | ++ |
| Malonate | ++ |
| L-Histidine | ++ |
| D-Malate | -- |
| L-Aspartate | ++ |
| L-Leucine | ++ |
| L-Tyrosine | ++ |
| β-Alanine | ++ |
| L-Glycine | ++ |
| Trans-Aconitate | ++ |
| D-Glucose | ++ |
| L-Tryptophane | ++ |
| Na-Acetate | ++ |
| Ethanol | ++ |
| L-Arginine | ++ |
| L-Ornithine | -- |
| DL 4-aminobutyrate | ++ |
| Other tests: | |
| Indole | -- |
| MR | -- |
| Triple sugar iron test | ++ |

In still another embodiment of the present invention, the strain *Acinetobacter baumannii* A30 is characterized as:

| Character | A. baumannii A30 |
|---|---|
| Growth at: | |
| 44° C. | ++ |
| 41° C. | ++ |
| 37° C. | ++ |
| 28° C. | ++ |
| Pigment production | NF |
| Acid from Glucose | NP |
| Gelatin Hydrolysis | ++ |
| Haemolysis | ++ |
| Citrate (Simmons) | ++ |
| Utilization of: | |
| DL-Lactate | ++ |
| L-Phenylalanine | -- |
| Phenyl acetate | -- |
| Malonate | ++ |
| L-Histidine | ++ |
| D-Malate | ++ |
| L-Aspartate | -- |
| L-Leucine | -- |
| L-Tyrosine | -- |
| β-Alanine | ++ |
| L-Glycine | ++ |
| Trans-Aconitate | -- |
| D-Glucose | ++ |
| L-Tryptophane | ++ |

-continued

| Character | A. baumannii A30 |
|---|---|
| Na-Acetate | ++ |
| Ethanol | ++ |
| L-Arginine | ++ |
| L-Ornithine | ++ |
| DL 4-aminobutyrate | ++ |
| Other tests: | |
| Indole | -- |
| MR | ++ |
| Triple sugar iron test | ++ |

In yet another embodiment of the present invention, the strain *Acinetobacter junii* A6 is characterized as:

| Characteristics | A. junii A6 |
|---|---|
| Growth at: | |
| 44° C. | ++ |
| 41° C. | ++ |
| 37° C. | ++ |
| 28° C. | ++ |
| Pigment production | -- |
| Acid from Glucose | -- |
| Gelatin Hydrolysis | ++ |
| Haemolysis | -- |
| Citrate (Simmons) | ++ |
| Utilization of: | |
| DL-Lactate | ++ |
| L-Phenylalanine | ++ |
| Phenyl acetate | ++ |
| Malonate | ++ |
| L-Histidine | ++ |
| D-Malate | -- |
| L-Aspartate | ++ |
| L-Leucine | ++ |
| L-Tyrosine | ++ |
| β-Alanine | ++ |
| L-Glycine | ++ |
| Trans-Aconitate | ++ |
| D-Glucose | ++ |
| L-Tryptophane | ++ |
| Na-Acetate | ++ |
| Oxalate | -- |
| Ethanol | ++ |
| L-Arginine | ++ |
| L-Ornithine | -- |
| DL 4-Aminobutyrate | ++ |
| Tween 20 | ++ |
| Tween 80 | ++ |
| Other tests: | |
| Indole | -- |
| MR | -- |
| VP | -- |
| Triple sugar iron test | ++ |

In another embodiment of the present invention, a bioinoculum for wheat plant comprises one or more strains selected from the group consisting of *Acinetobacter haemolyticus* A19, *Acinetobacter* genospecies A28, *Acinetobacter* genospecies A15, *Acinetobacter baumannii* A13, *Acinetobacter baumannii* A16, *Acinetobacter baumannii* A18, *Acinetobacter baumannii* A30, and *Acinetobacter junii* A6; and a carrier.

In one embodiment of the present invention, the carrier is lignite.

In another embodiment of the present invention, a method for promoting wheat plant growth comprises treating wheat seeds with the bioinoculum.

In yet another embodiment of the present invention, the bioinoculum comprises one or more strain selected from a group consisting of *Acinetobacter haemolyticus* A19, *Acinetobacter* genospecies A28, *Acinetobacter* genospecies A15, *Acinetobacter baumannii* A13, *Acinetobacter baumannii* A16, *Acinetobacter baumannii* A18, *Acinetobacter baumannii* A30, and *Acinetobacter junii* A6; and a carrier.

In yet another embodiment of the present invention, the *Acinetobacter* colonizes the seed during the treatment of the seed.

In still another embodiment of the present invention, the color of the leaf of the treated wheat plant becomes darker green.

In yet another embodiment of the present invention, the inflorescence and fruiting stages of the plant is reached in a time duration which is lessened by 10 days.

BRIEF DESCRIPTION OF THE ACCOMPANYING DRAWINGS

FIG. 1A: IAA production by four *Acinetobacter* genospecies isolated from rhizosphere of wheat: *A. baumannii* A13, *A.* genospecies 3 A15 and A28, and *A. junii* A6.

FIG. 1B: IAA production by four *Acinetobacter* genospecies: *A. haemolyticus* A19 and *A. baumannii* A18, A16 and A30, isolated from rhizosphere of wheat.

FIG. 2: TLC of purified IAA produced from *Acinetobacter* genospecies S. purified IAA: lane 30, *A. baumannii* (A30); lane 28, *A.* genospecies 3 (A28); lane 19, *A. haemolyticus* (A19); lane 18, *A. baumannii* (A18); lane 16, *A. baumannii* (A16); lane 15, *Acinetobacter* genospecies 3 (A15); lane 13, *A. baumannii* (A13); lane 6, *A. junii* (A6); lane I, Standard IAA.

FIG. 3: (A) IR spectrum of purified IAA *Acinetobacter* genospecies; (B) IR spectrum of standard IAA from Sigma (% T, percentage of transmission; $cm^{-1}$, wavelength in centimeters).

FIG. 4: $^1$H-NMR analysis of purified IAA from *Acinetobacter* genospecies.

FIG. 5: Effect of IAA produced by *Acinetobacter* genospecies on growth of wheat plant (A) Root and shoot length of 21-d wheat plant; (B) shoot width of 60-d wheat plant; (C) leaf width of 60-d wheat plant; (D) fruiting size and number of grains of 75-d wheat plant.

FIG. 6: Plasmid pUPI126 in IAA-producing *Acinetobacter* genospecies. Lane 1, *A. hemolyticus* (A19); Lane 2, *A. baumannii* (A13); Lane 3, *A. baumannii* (A16); lane 4, *Acinetobacter* genospecies 3 (A15); lane 5, *A. baumannii* (A18); lane 6, *A. junii* (A6); lane 7, *A.* genospecies 3 (A28).

The following examples are given by way of illustration of the present invention and therefore should not be construed to limit the scope of the present invention.

EXAMPLES

Culture Media

Five different culture media were used for isolation of *Acinetobacter* and other gram negative bacteria from wheat rhizosphere. The media used were as follows: violet red bile agar (VRBA) (Kleeberger et al, (1983)), and Cystine lactose electrolyte deficient medium (CLED, HiMedia laboratories Limited, Mumbai, India), for all gram negative bacteria; *Acinetobacter* minimal medium (AMM) (Juni, 1972), and Holton's selective medium (Holton, 1983), for growth of *Acinetobacter*. Standard plate count agar (SPCA), was used for estimation of total count of culturable bacteria present in all three samples (RP, RS, and NRS).

Isolation of *Acinetobacter* from Rhizosphere:

A dilution plate method (Subba Rao, 1986) was used for isolation of *Acinetobacter* and all other gram negative bacteria from wheat rhizosphere and rhizoplane. All types of colonies were isolated from four selective media and total bacterial counts were taken from SPCA. Colonies from VRBA, AMM, CLED and Holton's media were characterized by their morphological features and tentatively identified up to the genus level by gram character and morphology, motility, oxidase test, catalase test and capsule staining.

Chromosomal DNA Transformation Assay:

A chromosomal DNA transformation assay was carried out using naturally competent auxotrophic mutant *A. calcoaceticus* BD413 trpE27. Transformation was done by a modified method of Juni. In brief, the temperature used for lysis was 65° C. for 90 min.), using crude DNA (Juni, 1972), as well as purified DNA (Chen & Kuo, 1993) isolated from *Acinetobacter*. The growth of transformants of *Acinetobacter* on *Acinetobacter* Minimal Medium (AMM) without tryptophan was considered as a positive result of DNA transformation.

Identification of *Acinetobacter* Strains to Species Level:

*Acinetobacter* strains were classified to species level by the Bouvet and Grimont classification system (1986 & 1987). API 20NE was also employed for biotyping of *Acinetobacter* strains isolated from wheat rhizosphere (Towner & Chopade, 1987).

Detection of IAA Production in *Acinetobacter* spp:

IAA production was detected by two methods as described below:

Nitrocellulose Paper Assay:

All 37 *Acinetobacter* strains were tested by nitrocellulose paper assay (Bric et al 1991) for the production of IAA. Thirty-seven *Acinetobacter* strains were spot inoculated on LB medium supplemented with 5 mM tryptophan (LBT). The spot inoculated agar surface was overlaid with a nitrocellulose membrane filter and incubated at 28° C. for 48 h. The membrane filter was aseptically removed from the plate, after 48 h and transferred to Whatman filter paper No. 2. Salkowaski reagent 500 µl (2% of 0.5M $FeCl_3$ in 35% perchloric acid or $FeCl_3$ 2.025 g in 300 ml of conc. $H_2SO_4$ and 500 ml of distilled water) was added on the nitrocellulose paper and kept for 1-2 min. at room temperature. IAA production was indicated by a red ring around the colony.

Salkowaski Method:

In this method, (Gordons & Weber, 1951), thirty-seven *Acinetobacter* spp were grown at 28° C. in LB broth supplemented with 1 mg/ml of tryptophan. After 48 h of incubation, cells were harvested by centrifugation at 10000 rpm for 15 min. at room temperature and 1 ml of sample (supernatant) and 4 ml of Salkowaski reagent (Gordons & Weber, 1951) were mixed and allowed to react in the dark at room temperature for 30 min. One ml of uninoculated LBT and 4 ml of Salkowaski reagent was treated as a blank. Optical density (O.D) was checked at 540 nm. Red color formation was considered as positive evidence for IAA production. (Bric et al, 1991).

Time Course of IAA Producing *Acinetobacter* spp.:

IAA production by *Acinetobacter* strains at different growth phases was also studied. *Acinetobacter* strains were inoculated in LBT medium, incubated at 28° C. at 120 rpm and production of IAA was checked after every 2 h up to 108 h by the Salkowaski method.

Extraction and Purification of IAA by Preparative Thin Layer Chromatography (TLC):

IAA produced by *Acinetobacter* genospecies was purified by the method described by Koga et al (1991). In brief, all strains were grown in LBT medium until maximum IAA production became apparent. Culture broth (150 ml) was centrifuged at 8000 rpm (Remi, RMI2C, India) for 20 min at room temperature. The pH of the supernatant was adjusted to 7 (neutral extract). The supernatant was extracted with (1:1 volume) ethyl acetate. The aqueous phase was carefully separated and the pH was adjusted to 2.8 with HCl (acid extract). This acid extract was again extracted with (1:1 volume) ethyl acetate. Organic phases from both extractions were mixed together and evaporated on a rota-evaporator at 60° C. (Buchi, Switzerland) to obtain powdered IAA. At each phase of extraction, the Salkowaski test was done for the organic as well as the aqueous phase. Preparative TLC was run on the extracted samples using indole 3 acetic acid (Sigma, USA) as a standard, in methanol:chloroform (10:90) as a solvent system. The TLC was carried out on polygram G/UV 254 precoated aluminium sheets of 20×20 and 60 mm (Merck, Germany). The TLC spots were observed under UV (245 nm) and compared with standard IAA sample (Sigma, USA). IAA spots were scratched with a fine spatula. A sample with silica gel was collected in a clean glass bottle. The sample was dissolved in 2 ml of chloroform or ethyl acetate and filtered through cotton to remove silica. TLC was carried out on the sample to check the purity of the sample.

Identification of IAA by Infra Red (IR) Spectrum and Melting Point:

An IR spectrum of extracted IAA sample was taken using a Perkin Elmer 1600 FTIR Spectrophotometer. The spectra were recorded in nujol mull or in KBr pellets and expressed in wave number ($cm^{-1}$). The melting point of extracted IAA was tested on a Thomos Hoover melting point apparatus in degrees Celsius.

Analysis of IAA by $^1$H-NMR:

The purified IAA sample was analyzed by Mercury $^1$H-NMR (300 MHZ, Vavion, USA) and the peaks were identified for IAA. The $^1$H-NMR of standard IAA was also checked. The two $^1$H-NMR were compared. The purified IAA was dissolved in 25 µl of DMSO.

Effect of pH on IAA Production:

To study effect of pH on the production of IAA, buffered LBT broth was prepared in standard buffers such as acetate, phosphate and Tris-HCl (Gerhardt et al, 1994). The pH in the range of 4 to 9 was checked. The maximum IAA production phase at different pH was checked by Salkowaski test.

Effect of IAA Production by *Acinetobacter* spp. on Growth of Wheat Plant:

The effect of IAA production on the growth of wheat plant was tested by pot experiments. All eight *Acinetobacter* strains were grown separately in the following four media: i) LB, ii) LBT containing 1 mg/ml of tryptophan, iii) AMM, and iv) AMMT containing 1 mg/ml of tryptophan. LB and AMM were used as a control media and LBT and AMMT were used for IAA production. Eight *Acinetobacter* genospecies were inoculated in all four media and incubated at 120 rpm at 28° C. up to 48 h. The wheat seeds were surface sterilized by 2% $HgCl_2$ (Subba Rao, 1988) and washed with sterile distilled water for 6 to 7 times to remove $HgCl_2$ completely. After washing, the seeds were added in the above-mentioned cultures and kept on shakers at 120 rpm for 2 h at 28° C. After 2 h, wheat seeds were aseptically collected and inoculated in pots containing sterile soil. Wheat seeds mixed with uninoculated media as well as with distilled water were treated as a control. The pots were kept in sunlight and raised under close supervision. The growth of plants was observed everyday for 21 days. After 21 days, plants were carefully uprooted and root and shoot lengths were measured. The same experiment was simultaneously performed using large size pots up to a duration of 4 months, for the complete life cycle of the wheat plant.

Statistical Analysis:

Root length (RL) and shoot length (SL) were considered as the main parameters to the effect of IAA on wheat plants. Statistical analysis was done with the help of mean, standard deviation and analysis of variance (ANOVA) (Kulkarni et al, 1999).

Plasmid Isolation:

Eight strains were checked for the presence of plasmid(s). Plasmids were isolated by three different methods described by Kado and Lui (1981), Sambrook et al (1989) and Birnboim and Doly (1979). The presence of plasmid(s) was tested by 0.7% agarose gel electrophoresis in TAE buffer at 52 V for 6 to 8 h. Ethidium bromide stained gels were observed under a gel documentation system (Alpha Imager™ 2200 Documentation and Analysis System, Alpha Innotech Corporation, California, USA) and photographed. Molecular weight was determined by comparison with a 1 kb DNA ladder.

Plasmid Curing:

Plasmid curing was done for all eight strains of *Acinetobacter* genospecies using ethidium bromide (1024 µg/ml) and heat (52° C.) as described by Deshpande & Chopade (1994).

Transformation:

An *E. coli* HB101 (rif$^r$) mutant was used as a recipient for transformation. Plasmid DNA isolated from *A. haemolyticus* (A19) was used for transformation of DNA, as this strain showed good IAA production and also exhibited other interesting characteristics such as resistance to selenium, lead and tellurium (which were used as genetic markers for plasmid transformation), chitinase production and antimicrobial activity against plant as well as human pathogenic fingi and bacteria (Huddedar & Chopade, 2000). Transformation was carried out by preparing *E. coli* HB101 (rif$^r$) mutant cells by the $CaCl_2$ competence method (Sambrook et al, 1989) and competent *E. coli* cells were mixed with plasmid pUPI126 DNA (10 µl). The transformants were selected and checked for IAA production by the Salkowaski test. A parent recipient *E. coli* HB101 (rif$^r$) mutant was used as a control.

Results:

Isolation, Identification and Confirmation of *Acinetobacter* Genospecies:

Colonies showing mucoid character were selected and tested for gram character and morphology, motility, presence of capsule, oxidase and catalase production. Gram negative, coccobacilli, non-motile, oxidase negative, catalase positive and capsulated strains were considered as tentative *Acinetobacter* spp and confirmed by chromosomal DNA transformation assay. Thirty-seven *Acinetobacter* strains isolated from five stages of wheat plant were confirmed as genuine Acinetobacters. *Acinetobacter* strains were identified to species level on the basis of biochemical tests. These Acinetobacters were not biotypable by the API 20NE system. Eight IAA producing strains were identified as *A. baumannii* (A18, A16, A13 and A30), *A. haemolyticus* (A19), *A. junii* (A6) and *A.* genospecies 3 (A15, A28) (Table 1).

Production of IAA by *Acinetobacter* Strains:

All thirty-seven Acinetobacters were tested for IAA production by nitrocellulose paper assay. It was observed that among thirty-seven *Acinetobacter* strains only eight *Acinetobacter* strains showed a red ring around bacterial colony growth within 1 min on addition of Salkowaski reagent. IAA production for these eight *Acinetobacter* strains was also detected by the Salkowaski method, and the development of red color indicated the presence of IAA. One ml distilled water and 4 ml of Salkowaski reagent was taken as a negative control.

Time Course of IAA Producing *Acinetobacter* spp:

It was found that five strains of *Acinetobacter* such as *A. haemolyticus* (A19), *A. baumannii* (A18, A16, A13) and *A.* genospecies 3 (A15), showed maximum LAA production in the early stationary phase (48 h). *A. junii* (A6) showed maximum IAA production in the log phase (24 h), and *A.* genospecies 3 (A28) and *A. baumannii* (A30) showed maximum IAA production in the late stationary phase (60 and 72 h). FIGS. 1 A and B, represent the growth phase with maximum IAA production by each *Acinetobacter* spp.

Extraction and Purification of IAA by TLC:

Extraction of IAA was done by ethyl acetate. The Salkowaski test done at each step of the extraction showed that only the organic phase contained IAA. The dry powder obtained after evaporation of ethyl acetate (Bouchi evaporater) showed the presence of IAA. The powder was further fractionated by preparative TLC. The band pattern of purified IAA was comparable with standard IAA. (FIG. 2). It was observed that when these TLC bands were scratched and again tested by TLC, a single band was noted as that of standard IAA with $R_f$ value 0.5. The amount of auxin found in the culture filtrate was 4 mg/Lit.

Identification of IAA by IR Spectrum and by Melting Point:

The IR spectrum of the purified IAA showed an OH frequency at 3384.9 cm$^{-1}$ and C=O frequency at 1698.4 cm$^{-1}$ (FIG. 3). The IR spectrum of standard IAA also showed the same results. The melting point of the purified IAA was found to be 168° C., which is the same as standard IAA.

Analysis of IAA by $^1$H-NMR:

The $^1$H-NMR of the eight purified LAA samples was found to be same as the $^1$H-NMR of standard IAA (FIG. 4). The first peak from right is of acid, value 9.0 δ bs (—OH). Lateral peaks are of protons having values 7.8 δ d 1H ($C_8$H), 7.5 δ d 1H ($C_5$H), 7.31 δ d 1H ($C_2$H) and 7.07 δ m 2H($C_6$ and $C_7$H). The middle large peak is DMSO having a value of 3.04 δ S (d$^6$), and moisture. The next peak is of carbon and hydrogen, having a value of 2.59 δ S 2H (—$CH_2$—). The last peak is the peak of the internal standard, tetramethyl-silnate (TMS), value 0.08.

Effect of pH on IAA Production:

It was observed that at acidic pH (pH 4 and 5) *Acinetobacter* genospecies could not grow. The growth and IAA production was observed from pH 6 to pH 9 and found that pH 7 was the optimum for IAA production by *A. baumannii* (A16, A18, A30), *A. genospecies* 3 (A15), *A. haemolyticus* (A19), and *A. junii* (A6). The two strains *A. baumannii* (A13) and *A. genospecies* 3 (A28) showed optimum IAA production at pH 9 (Table 2).

Effect of IAA Produced by *Acinetobacter* on Growth of Wheat Plant:

Statistical analysis showed significant difference in root and shoot length of test wheat plants (21 days) as compared to control plants (Table 3). A similar difference was observed when the same experiment was performed using large size pots (Table 4). It was observed that there was a difference in color of the leaves of the control and inoculated plants. Leaf color of plants inoculated with *Acinetobacter* spp. was dark green as compared to the pale green of the control. Interestingly, the shoot width of the inoculated plants was found to be almost double the control. It was also observed that development of inflorescence stage (flowering stage) and fruiting stages were observed 10 days earlier in inoculated plants as compared to the control. (FIG. 5).

Plasmid Isolation:

All eight *Acinetobacter* strains contained one plasmid of the molecular weight 40 kb. All three methods of plasmid DNA isolation showed the presence of only one plasmid in all eight strains. The plasmid was designated as pUPI126.

Plasmid Curing:

Plasmid pUPI126 was not cured by ethidium bromide, even at a concentration of 1024 µg/ml and heat (52° C.).

Transformation of Plasmid pUPI126:

Plasmid pUPI126 showed resistance to selenium, tellurium and lead and was transformed to *E. coli* HB101 rif$^r$ mutant at a frequency of $5\times10^{-5}$. Along with IAA, selenium, tellurium and lead were also co-transferred almost at the same frequency. Transformants showed IAA production as checked by the Salkowaski test. The color developed was pink as compared to the red color developed by the original host *A. haemolyticus* A19 strain. The negative control, *E. coli* HB101 (rif$^r$) mutant, did not show any color formation with Salkowaski reagent. Plasmid pUPI126 was isolated from transformants and observed by 0.7% agarose gel electrophoresis.

The novel plasmid pUPI126 encodes IAA production, along with resistance to tellurium, selenium, arsenate and kanamycin. The cultures containing plasmid pUPI126 were submitted to the National Collection of Industrial Microorganisms (NCIM), at the National Chemical Laboratory (NCL), Pune, India. These cultures are available for experiment. The names and NCIM designation numbers of the submitted strains are as follows:

|      | Name of Bacteria              | NCIM Number |
|------|-------------------------------|-------------|
| I.   | *A. haemolyticus* A19 (pUPI126)  | NCIM 5155   |
| II.  | *A. genospecies* 3 A28 (pUPI126) | NCIM 5159   |
| III. | *A. genospecies* 3 A15 (pUPI126) | NCIM 5151   |
| IV.  | *A. baumannii* A13 (pUPI126)     | NCIM 5158   |
| V.   | *A. baumannii* A16 (pUPI126)     | NCIM 5156   |
| VI.  | *A. baumannii* A18 (pUPI126)     | NCIM 5157   |
| VII. | *A. baumannii* A30 (pUPI126)     | NCIM 5154   |
| VIII.| *A. junii* A6 (pUPI126)          | NCIM 5153.  |

*Acinetobacter haemolyticus* strain A19 was deposited pursuant to the Budapest Treaty in the Microbial Type Culture Collection & Gene Bank, Institute of Microbial Technology, Sector 39-A, Chandigarh-160 063, India, on Jun. 6, 2005, under accession number MTCC 5218.

The eight *Acinetobacter* strains are novel. It is important to note that *Acinetobacter* spp. from the rhizosphere of no plant has been isolated and studied in detail for its characteristics. For comparison, soil isolates were taken according to Bouvet and Grimont (1986, 1987) and *A. calcoaceticus* MTCC127. Differences in the results indicate that the *Acinetobacter* strains are distinct from known *Acinetobacter*. The detailed characteristics of these strains is given as follows

TABLE 1

Identification of IAA producing *Acinetobacter* spp isolated from rhizosphere of wheat.

| Characteristics     | *A. baumannii* (Std)* | *A. baumannii* A13 | *A. baumannii* A16 | *A. baumannii* A18 | *A. baumannii* A30 |
|---------------------|----------------------|--------------------|--------------------|--------------------|--------------------|
| Growth at:          |                      |                    |                    |                    |                    |
| 44° C.              | ++                   | ++                 | ++                 | ++                 | ++                 |
| 41° C.              | ++                   | ++                 | ++                 | ++                 | ++                 |
| 37° C.              | ++                   | ++                 | ++                 | ++                 | ++                 |
| 28° C.              | ++                   | ++                 | ++                 | ++                 | ++                 |
| Pigment production  | ND                   | NP                 | Brown              | Yellow             | NF                 |
| Acid from Glucose   | ++                   | NP                 | NP                 | ++                 | NP                 |
| Gelatin Hydrolysis  | --                   | --                 | --                 | --                 | ++                 |
| Haemolysis          | --                   | ++                 | --                 | --                 | ++                 |
| Citrate (Simmons)   | ++                   | ++                 | ++                 | ++                 | ++                 |
| Utilization of:     |                      |                    |                    |                    |                    |
| DL - Lactate        | ++                   | ++                 | ++                 | ++                 | ++                 |
| L - Phenylalanine   | ++                   | ++                 | ++                 | ++                 | --                 |
| Phenyl acetate      | ++                   | ++                 | --                 | ++                 | --                 |
| Malonate            | ++                   | ++                 | ++                 | ++                 | ++                 |
| L - Histidine       | ++                   | ++                 | ++                 | ++                 | ++                 |

TABLE 1-continued

Identification of IAA producing *Acinetobacter* spp isolated from rhizosphere of wheat.

| Characteristics | A. baumannii (Std)* | A. baumannii A13 | A. baumannii A16 | A. baumannii A18 | A. baumannii A30 |
|---|---|---|---|---|---|
| D - Malate | ++ | ++ | ++ | -- | ++ |
| L - Aspartate | ND | ++ | ++ | ++ | -- |
| L - Leucine | ++ | ++ | ++ | ++ | -- |
| L - Tyrosine | ++ | ++ | ++ | ++ | -- |
| β- Alanine | ++ | ++ | ++ | ++ | ++ |
| L - Glycine | ND | ++ | ++ | ++ | ++ |
| Trans-Aconitate | ++ | -- | ++ | ++ | -- |
| D- Glucose | ND | ++ | ++ | ++ | ++ |
| L - Tryptophane | -- | ++ | ++ | ++ | ++ |
| Na - Acetate | ND | ++ | ++ | ++ | ++ |
| Ethanol | ++ | ++ | ++ | ++ | ++ |
| L - Arginine | ++ | ++ | ++ | ++ | ++ |
| L - Ornithine | ++ | ++ | ++ | -- | ++ |
| DL 4-aminobutyrate | ++ | ++ | ++ | ++ | ++ |
| Other tests: | | | | | |
| Indole | ND | -- | -- | -- | -- |
| MR | ND | -- | -- | -- | ++ |
| Triple sugar iron test | ND | ++ | ++ | ++ | ++ |

(std)*: From Bouvet and Grimont (1986, 1987). This was done as per Bouvet and Grimont (1986 & 1987). Besides these some additional tests were done.
--: negative,
++: positive,
NP: not produced,
ND: Not detected.
Bold indicates differential tests.

TABLE 2

| Characteristics | A. genospecies 3 (Std)* | A. genospecies A15 | A. genospecies 3 A28 |
|---|---|---|---|
| Growth at: | | | |
| 44° C. | -- | -- | -- |
| 41° C. | ++ | ++ | ++ |
| 37° C. | ++ | ++ | ++ |
| 28° C. | ++ | ++ | ++ |
| Pigment production | -- | Pink | Pink |
| Acid from Glucose | ++ | ++ | ++ |
| Gelatin Hydrolysis | -- | -- | -- |
| Haemolysis | -- | -- | -- |
| Citrate (Simmons) | ++ | ++ | ++ |
| Utilization of: | | | |
| DL-Lactate | ++ | ++ | ++ |
| L-Phenylalanine | ++ | ++ | ++ |
| Phenyl acetate | ND | ++ | -- |
| Malonate | ++ | ++ | ++ |
| L-Histidine | ++ | ++ | ++ |
| D-Malate | ++ | ++ | ++ |
| L-Aspartate | ++ | ++ | ++ |
| L-Leucine | ND | ++ | ++ |
| L-Tyrosine | ++ | ++ | ++ |
| β-Alanine | ++ | ++ | ++ |
| L-Glycine | ND | ++ | ++ |
| Trans-Aconitate | ++ | ++ | ++ |
| D-Glucose | ND | ++ | ++ |
| L-Tryptophane | ND | ++ | ++ |
| Na-Acetate | ND | ++ | ++ |
| Ethanol | ++ | ++ | ++ |
| L-Arginine | ++ | ++ | ++ |
| L-Ornithine | ++ | ++ | ++ |
| DL 4-Aminobutyrate | ++ | ++ | ++ |
| Other tests: | | | |
| MR | ND | ++ | ++ |
| VP | ND | -- | -- |
| Triple sugar ion test | ND | ++ | ++ |

(std)*: From Bouvet and Grimont (1986,1987).
*This was done as per Bouvet and Grimont (1986 & 1987). Besides these some additional tests were done.
--: negative,
++: positive,
NP: not produced,
ND: Not detected.
Bold indicates Differential test.

TABLE 3

| Characteristics | A. haemolyticus (Std)* | A. haemolytivus A19 | A. junii (std)* | A. junii A6 |
|---|---|---|---|---|
| Growth at: | | | | |
| 44° C. | -- | ++ | -- | ++ |
| 41° C. | ++ | ++ | ++ | ++ |
| 37° C. | ++ | ++ | ++ | ++ |
| 28° C. | ++ | ++ | ++ | ++ |
| Pigment production | -- | Yellow | -- | -- |
| Acid from Glucose | ++ | ++ | -- | -- |
| Gelatin Hydrolysis | ++ | ++ | -- | ++ |
| Haemolysis | ++ | ++ | -- | -- |
| Citrate | ++ | ++ | ++ | ++ |

TABLE 3-continued

| Characteristics | A. haemolyticus (Std)* | A. haemolytivus A19 | A. junii (std)* | A. junii A6 |
|---|---|---|---|---|
| (Simmons) Utilization of: | | | | |
| DL - Lactate | -- | ++ | ++ | ++ |
| L - Phenylalanine | -- | ++ | -- | ++ |
| Phenyl acetate | ++ | ++ | -- | ++ |
| Malonate | -- | ++ | -- | ++ |
| L - Histidine | ++ | ++ | ++ | ++ |
| D - Malate | ++ | ++ | ++ | -- |
| L - Aspartate | -- | -- | ++ | ++ |
| L - Leucine | -- | -- | -- | ++ |
| L - Tyrosine | -- | ++ | ++ | ++ |
| β - Alanine | -- | ++ | -- | ++ |
| L - Glycine | ND | ++ | ND | ++ |
| Trans-Aconitate | -- | -- | -- | ++ |
| D - Glucose | ND | ++ | ND | ++ |
| L - Tryptophane | ND | ++ | ND | ++ |
| Na - Acetate | ND | ++ | ND | ++ |
| Oxalate | ND | ++ | ND | -- |
| Ethanol | ++ | ++ | ++ | ++ |
| L - Arginine | ++ | ++ | ++ | ++ |
| L - Ornithine | ++ | ++ | -- | -- |
| DL 4-Aminobutyrate | ++ | ++ | ++ | ++ |
| Tween 20 | ND | ++ | ND | ++ |
| Tween 80 | ND | ++ | ND | ++ |
| Other tests: | | | | |
| Indole | ND | -- | ND | -- |
| MR | ND | -- | ND | -- |
| VP | ND | -- | ND | -- |
| Triple sugar iron test | ++ | ++ | ++ | ++ |

(std)*: From Bouvet and Grimont (1986, 1987).
*This was done as per Bouvet and Grimont (1986 & 1987). Besides these some additional tests were done.
--: negative,
++: positive,
NP: not produced,
ND: Not detected.
Bold indicates differential test.

From Table 1, it was found that at least 10 tests for *Acinetobacter baumannii*, isolated from rhizosphere of wheat gave different results from the standard *A. baumannii*. Table 2, indicates that 6 tests for *A.* genospecies 3, isolated from the rhizosphere of wheat, gave different results from standard *A.* genospecies 3. Table 3, indicates that 6 tests from *A. haemolyticus* and 8 tests for *A. junii*, isolated from the rhizosphere of wheat, gave different results from standard *A. haemolyticus* and *A. junii*, respectively. Thus, on the basis of these new characteristics, these strains are novel.

The present invention involves an inventive step because though microbes in the rhizosphere of plants are able to produce IAA, each microbe does not necessarily produce IAA. In case of *Acinetobacter*, we studied the presence and role of *Acinetobacter* in the rhizosphere of wheat and proved experimentally that *Acinetobacter* is significantly present in the rhizosphere of wheat. The significant presence of *Acinetobacter* motivated us to find the role of *Acinetobacter* in the rhizosphere of wheat. After much experimental work, we proved that *Acinetobacter* is able to produce IAA, and production of IAA is encoded by plasmid pUPI126, which is the first report on plasmid-encoded IAA production in the genus *Acinetobacter*.

Use of the Microbes as Bioinoculants

The following experiment was done to prove that *Acinetobacter* may be used as a bioinoculant. This is additional work which we have performed to confim the effect of IAA produced by *Acinetobacter* on wheat plants.

i. Preparation of *Acinetobacter* Bioinoculum:

*Acinetobacter* bioinoculum was prepared by using lignite as a carrier. Lignite was sterilized at 121° C. for 1 h. After 1 h autoclaving, the lignite was allowed to cool. *A.* genospecies 3 A28 wild and mutant (A28.1) and *A. haemolyticus* A19 wild and rif$^r$ mutant (A19.1) were inoculated in 500 ml of Luria broth and the flasks were incubated at 120 rpm for 48 h at 30° C. After 48 h the flasks were removed from incubation, sterile lignite and cultures of *A.* genospecies 3 A28 wild and rifampicin-resistant mutant as well as *A. haemolyticus* A19 wild and rif$^r$ mutant were aseptically mixed separately in the proportion of 500 mg lignite and 250 ml of each culture, using sterile gloves. The mixture of each bioinoculum was properly labeled and incubated at 30° C. for 24 h in sterile plastic bags in two sets. These sets were then used in field treatments of bioinoculum to wheat plants. (Subba Roq, 1988).

ii. Field Trials of *Acinetobacter* Bioinoculum for Wheat Plant:

Field trials of a novel bioinoculum of *A.* genospecies 3 A28 wild and rif$^r$ mutant (A28.1), as well as *A. haemolyticus* A19 wild and rif$^r$ mutant (A19.1), were conducted on wheat plants. The variety of wheat plant was HD 2189. Bioinoculum and chemical fertilizer treatments were given in two different fields, first in an experimental field of Mahatma Phule Agriculture College, Shivajinagar, Pune and second in a field of a local farmer at Hadapsar, Pune. The following types of the treatments were given to the wheat seeds with and without application of bioinoculum, and by using different doses of chemical fertilizers
  a) Treatment 1: Wheat seeds were treated with only the bioinoculum of *A.* genospecies 3 A28 wild.
  b) Treatment 2: Wheat seeds were treated with only the bioinoculum of *A. haemolyticus* A19 wild.
  c) Treatment 3: Wheat seeds were treated with only the bioinoculum of *A.* genospecies 3 A28 mutant.
  d) Treatment 4: Wheat seeds were treated with only the bioinoculum of *A. haemolyticus* A19 mutant.
  e) Treatment 5: Wheat seeds were treated with the bioinoculum of *A.* genospecies 3 A28 wild and a half dose of fertilizer as in step (b) above.
  f) Treatment 6: Wheat seeds were treated with the bioinoculum of *A. haemolyticus* A19 wild and a half dose of fertilizer as in step (b) above.
  g) Treatment 7: Wheat seeds were treated with the bioinoculum of *A.* genospecies 3 A28 mutant and a half dose of fertilizer as in step (b) above.
  h) Treatment 8: Wheat seeds were treated with the bioinoculum of *A. haemolyticus* A19 mutant and a half dose of fertilizer as in step (b) above.
  i) Treatment 9: Wheat seeds treated with standard *Azotobacter* bioinoculum (provided by Mahatma Phule Agriculture College, Shivajinagar, Pune).
  j) Treatment 10: Wheat seeds treated with a standard *Azotobacter* bioinoculum. (provided by Mahatma Phule Agriculture College, Shivajinagar, Pune) with a half dose of fertilizer as in step (b) above.
  k) Treatment 11: Wheat seeds treated with a standard *Azospirillum* bioinoculum (provided by Mahatma Phule Agriculture, College, Shivajinagar, Pune).

l) Treatment 12: Wheat seeds treated with a standard *Azospirillum* bioinoculum (provided by Mahatma Phule Agriculture, College, Shivajinagar, Pune) with a half dose of fertilizer as in step (b) above.
m) Control 1: Wheat seeds were treated without bioinoculum and chemical fertilizer.
n) Control 2: Wheat seeds were treated without bioinoculum and with half dose of chemical fertilizer such as Urea 0.6 kg/100 m$^2$, and single super phosphate 1.3 kg/100 m$^2$.

After these treatments, the wheat plants were observed for different growth parameters.

iii. Effect of Colonization of *Acinetobacter* to the Wheat Plants in the Field:

Colonization study is important to indicate that the *Acinetobacter* bioinoculum is effectively colonizing the roots of the wheat plants. This confirms the plant growth promoting effect of *Acinetobacter* bioinoculum on wheat plants.

Rif$^r$ mutants isolated from *A*. genospecies 3 A28.1 and *A. haemolyticus* A19.1 were mainly used for this purpose. Colonization by these mutants was observed at 4 major life stages of wheat plants, after (i.) 30 days, (ii.) 45 days, (iii.) 60 days and (iv.) 75 days. At each of these 4 life stages, wheat plants treated with only mutants of *A*. genospecies 3 A28 and *A. haemolyticus* A19 were uprooted and the roots were washed thoroughly 5-6 times with sterile distilled water. Roots were then cut into small pieces of 2-3 cm, weighed to 1 g, and kept in sterile saline (0.85%) on a shaker for half an hour. Serial dilutions were then made in the sterile saline and the dilutions plated out on Luria agar containing 100 μg/ml of rifampicin. Plates were incubated at 28° C. for 48-60 h. A colony count was taken after 60 h. The experiment was done in duplicate. The colonization of wheat root was also carried out by a root mapping method (Brown, 1962). Wheat roots were mapped on Luria agar containing 100 g/ml of rifampicin. Plates were incubated at 28° C. for 24-48 h and observed for colonization.

iv. Effect of *Acinetobacter* Bioinoculum on Wheat Plant:

The effect of *Acinetobacter* bioinoculum on wheat plant was observed considering the following parameters.
 a. Measurement of shoot length of wheat plants (total height of plant).
 b. Measurement of number of tillers of wheat plants.
 c. Measurements of width of leaves of wheat plants.

Significant differences between controls and different treatments was calculated by employing statistical methods such as, the Mean, Standard Deviation, ANOVA and T-test.

The inventiveness of the invention can be further substantiated by the fact that it is not true that *Pseudomonas* is producing IAA. *Acinetobacter* is producing it. In fact, for the first time, we have proved that the genus *Acinetobacter* is able to produce IAA and take part in plant growth promotion. The behavior of *Pseudomonas* is not a motivation/clue. In fact, in order to understand the role of *Acinetobacter* in plant growth promotion, we proposed a hypothesis. This hypothesis was proved experimentally by us. For this, about 800 references were studied in detail. By studying the biology of *Acinetobacter* from the literature and our previous large number of publications on *Acinetobacter*, we formulated a hypothesis that *Acinetobacter* spp. may be present in the rhizosphere of wheat and may have important properties. It may exhibit characteristics like antibiotic and metal resistance, antibiotic, bioemulsifier and IAA production to promote plant growth. It may carry plasmids encoding some of the special features and it may help to understand the role of *Acinetobacter* in rhizosphere of wheat. Much creativity, hard work, thinking and experimental planning has made it possible to prove this hypothesis.

TABLE 4

Effect of pH on IAA production by *Acinetobacter* genospecies.

| pH | A. genospecies 3 | | A. baumannii | | | | A. junii | A. haemolyticus |
|---|---|---|---|---|---|---|---|---|
|    | A15 | A28 | A16 | A18 | A30 | A13 | A6 | A19 |
| 6 | 0.02 | 0.08 | 0.07 | 0.81 | 1.23 | 0.06 | 1.46 | 1.22 |
| 7 | 0.13 | 0.14 | 0.32 | 1.10 | 1.90 | 1.45 | 1.43 | 1.95 |
| 8 | 0.11 | 0.23 | 0.21 | 0.92 | 1.12 | 1.46 | 1.35 | 1.01 |
| 9 | 0.10 | 0.35 | 0.29 | 0.58 | 0.88 | 1.52 | 1.28 | 0.55 |

* OD measured at 540 nm.
* At pH 4 and 5 there was no growth of *Acinetobacter* genospecies hence there was no IAA production.

TABLE 5

Effect of IAA producing *A*. genospecies on root length and shoot length of 21 days wheat plant by ANOVA Test.

| Source | Root Length (cm) | | | | Shoot Length (cm) | | | |
|---|---|---|---|---|---|---|---|---|
|    | Df | SS | MS | F | df | SS | MS | F |
| Medium | 4 | 2193.7 | 548.4 | 33.2 | 4 | 3407.8 | 851.9 | 42.5 |
| Bacteria | 8 | 3900.4 | 487.5 | 29.5 | 8 | 1770.0 | 221.2 | 11.0 |

TABLE 5-continued

Effect of IAA producing *A. genospecies* on root length
and shoot length of 21 days wheat plant by ANOVA Test.

| | Root Length (cm) | | | | Shoot Length (cm) | | | |
|---|---|---|---|---|---|---|---|---|
| Source | Df | SS | MS | F | df | SS | MS | F |
| Interaction | 24 | 3814.7 | 158.9 | 9.6 | 24 | 2669.7 | 111.2 | 5.5 |
| Error | 1069 | 17622.6 | 16.4 | | 648 | 154726.4 | 20.0 | |
| Total | 1105 | 27,531.4 | | | 684 | | | | df: degree of freedom,
SS: sum of squares,
MS: mean squares,
F: F-test., Medium: AMM, LB, AMMT and LBT,
Bacteria: *Acinetobacter genospecies*,
Interaction: Interactions takes place between bacteria—bacteria & media and bacteria.

TABLE 6

Effect of IAA produced by *Acinetobacter genospecies* on root and
shoot length of wheat plant at ripened fruiting stage (75d)[a].

| | Root length (cm) | | Shoot length (cm) | |
|---|---|---|---|---|
| Genospecies | Mean | SD | Mean | SD |
| *A. baumannii* | | | | |
| A18 | 36.7 | 5.02 | 40.1 | 0.1 |
| A13 | 32.3 | 2.5 | 36.9 | 5.7 |
| A30 | 32.4 | 4.8 | 35.1 | 4.8 |
| A16 | 37.2 | 2.3 | 33.5 | 5.5 |
| *A. haemolyticus* | | | | |
| A19 | 35.3 | 3.5 | 41.7 | 2.8 |
| *A. junii* | | | | |
| A6 | 35.6 | 2.5 | 40.1 | 0.1 |
| *A. genospecies* | | | | |
| 3 | 37.2 | 4.3 | 40.3 | 0.3 |
| A15 | 41.4 | 2.1 | 42.6 | 2.08 |
| A28 | | | | |

[a]Values are based on three sets of experiments.
SD: Standard Deviation.

*Acinetobacter* is commonly found in soil (Baumann, 1968; Dhakephalkar & Chopade 1994[b]). Therefore it was logical to believe that it may be present in rhizosphere. However there is no report on the presence of *Acinetobacter* in the rhizosphere of plants including wheat plant, which is an economically important plant. There is only a passing statement on the presence of *Acinetobacter* in the wheat rhizosphere (Kleeberger et al, 1983). *Acinetobacter* is a relatively recently studied group of microorganisms. This is because previously this bacteria was known by 40 different names and hence there has been much confusion about the systematics of *Acinetobacter* spp. (Henriksen, 1973). With the development of a chromosomal DNA transformation assay by Juni (1972 & 1978), a genuine method of confirmation of *Acinetobacter* was developed. This assay is specific only for *Acinetobacter* genospecies. Based on this assay, the authenticity of the genus *Acinetobacter* was established (Juni, 1972 & 1978).

At present, the systematics of *Acinetobacter* is well defined and it consists of 21 genospecies (John, et al 1994, Bouvet & Grimont 1986 & 1987). The aim of this study was to find out the effect of IAA production by *Acinetobacter* strains on the overall life cycle of wheat plant.

Our work in this area was done systematically because of the routine use of chromosomal DNA transformation assay for confirmation of genus *Acinetobacter* (Juni, 1972; Deshpande & Chopade, 1994). Interestingly, all 37 isolates of *Acinetobacter* were confirmed by this assay. It is important to note that, out of 21 genospecies, only five *Acinetobacter* genospecies were detected from rhizosphere of wheat. Our findings have revealed that *Acinetobacter* is present in the rhizosphere of wheat in significant number (Huddedar & Chopade, 2000). This finding gave us the most valuable clue that *Acinetobacter* may have some role in the wheat rhizosphere. It should be noted that *Acinetobacter* is not a plant pathogen. To determine its role in the plant growth promotion, we did screening of *Acinetobacter* spp for IAA production. It is important to note that until now there is no report on the production of IAA in the genus *Acinetobacter* from wheat rhizosphere. The determination of the IAA producing capacity of a microorganism is useful in its identification, and provides a valuable marker when examining the physiological role or ecological significance of IAA in the establishment and persistence of organism in the rhizosphere (Bric et al, 1988). As compared to other IAA producing bacteria, production of IAA with respect to the growth phase of *Acinetobacter* is similar in that it produced IAA in the stationary phase, but *A. junii* (A6) produced IAA in the log phase. Interestingly the IAA production by *Acinetobacter* is qualitatively strong as it takes a dark red color within one minute when it reacts with Salkowaski reagent on nitrocellulose paper.

The TLC of extracts clearly showed the presence of IAA in all eight *Acinetobacter* genospecies (FIG. 2). The $^1$H-NMR, IR and melting point of extracted samples matched with the standard IAA. We found that pH also affected the IAA production and neutral pH (7) was found to be best for production of IAA in the four *Acinetobacter* genospecies *A.* genospecies 3, *A. baumannii, A. junii* and *A. haemolyticus* (A15, A16, A18, A13, A6 and A19). Out of eight, in two *Acinetobacter* genospecies, *A. baumannii* A13 and *A.* genospecies 3 A28, IAA was produced in maximum amount at alkaline pH as compared to acidic pH. This fact has ecological significance as the pH of clay soil used for cultivation of wheat in Maharashtra, India, is alkaline (pH 8 to 10). The effect of IAA on plant root, shoot length and width, fruiting capacity and health of the plants as compared with control plants clearly indicated that IAA is produced by *Acinetobacter* and it is directly involved in plant growth promotion. The *Acinetobacter* genospecies grown in AMMT or LBT promoted maximum growth of wheat plants in pots since the growth media was supplemented with tryptophan, the precursor for IAA production. The *Acinetobacter* strains grown in AMM and LB promoted less growth of plants, as there was lack of tryptophan. This observation indicates that plant growth was definitely promoted by IAA produced from *Acinetobacter* genospecies. Similarly the effect of an inoculation with IAA producing three *Pseudomonas* and one *Acinetobacter* on root growth, resulting in increased shoot growth of maize plant, has been demonstrated (Lippmann et al, 1995).

Plasmid isolation and transformation of plasmid pUPI126 to *E. coli* HB101 (Rif<sup>r</sup>) mutant provided evidence that production of IAA and resistance to selenium, tellurium and lead genes are encoded on the plasmid pUPI126 in *Acinetobacter haemolyticus* A19, and that *E. coli* HB101 transformants also produced IAA in stationary phase. Our findings are very similar to previously published results of *Pseudomonas savastanoi* in which IAA producing genes are also encoded on plasmid pIAA1 (Comai & Kosuge, 1982; Costacurta & Vanderleyden, 1995). To the best of our knowledge, this is the first report of the IAA production in the genus *Acinetobacter*. It is observed that plasmid pUPI126 was not cured either by ethidium bromide or heat which suggests that this plasmid is very stable in its original host *Acinetobacter*. Plasmid transfer and behavior is well established in *Acinetobacter* (Chopade et al, 1985; Deshpande & Chopade 1994; Naik et al, 1994). It would be worthwhile to investigate the behavior of this plasmid pUPI126 in the rhizosphere microorganisms.

Besides indole acetic acid (IAA) encoded by plasmid pUPI126, other characteristics, such as production of hormones, such as cytokines (as reported in plasmid pP4TH in *Erwinia herbicola* pv. *Phypsophiloe* (Clark, et al, 1993)), are encoded by plasmid and warrant further investigation. This work has indeed established the role of *Acinetobacter* in wheat rhizosphere. It is expected that this work will provide stimulus to the work on *Acinetobacter* plant interactions in variety of economically important plants. The present study has successfully shown the effect of IAA on the growth of wheat plant. Large size pot experiments have confirmed this observation. Besides enhancement of growth of wheat plant, the flowering (inflorescence) and fruiting stages of the life cycle were reached about 10 days earlier, and persisted longer than the controls. Overall, health of the wheat plant was very much improved as compared to control. This indicates the potential of *Acinetobacter* as a novel bioinoculant for wheat. Further studies on cloning of IAA genes and their regulation, the pathway of IAA biosynthesis, and field studies on effect of IAA produced by different *Acinetobacter* genospecies on growth and yield of wheat plant and development of bioinoculant are in progress.

CONCLUSIONS

This is the first report on plasmid encoded LAA production in the genus *Acinetobacter*. From this result, the role of *Acinetobacter* in wheat rhizosphere becomes very clear. It proves that *Acinetobacter* has a symbiotic interaction with wheat plant and able to stimulate wheat plant growth. Thus, this bacteria can be further used to increase in yield of wheat plant.

REFERENCES

1. Arshad, M and W. T. Jr. Frankenberger. (1991). Microbial production of plant hormones. Plant Soil., 133: 1-15.
2. Baldi, B. G., B. R. Maher, J. P. Slovin and J. D. Choen. (1991). Stable isotope labeling in vitro of D and l tryptophan pools in *Lemna gibba* and low incorporation of label in to indole 3 acetic acid Plant Physiol., 95:1203-1223.
3. Bashan, Y., M. Singh, and H. Leveanony. (1989). Contribution of *Azospirillum brasilense* Cd to growth of tomato seedling is not through nitrogen fixation. Can. J. Bot., 67: 2429-2444.
4. Baumann, P. (1968). Isolation of *Acinetobacter* from soil and water. J. Bacteriol., 96: 39-42
5. Birnboim, H. C. and, J. Doly. (1979). A rapid alkaline extraction procedure for screening recombinant plasmid DNA. Nucleic Acid Research. 7: 1513-1523.
6. Bouvet, P. J. M. and P. A. D. Grimont. (1986). Taxonomy of genus *Acinetobacter* with the recognition of *Acinetobacter baumannii* sp. nov., *Acinetobacter haemolyticus* sp. Nov., *Acinetobacter johnsonii* sp. Nov., and *Acinetobacter junii* sp., nov and emended descriptions of *Acinetobacter calcoaceticus* and *Acinetobacter lwoffii*. Ann. Inst. Pasture/Microbiol, 138: 569-578.
7. Bouvet, P. M. and P. A. D. Grimont. (1987). Identification and biotyping of clinical isolates of *Acinetobacter*. Int. J. Syst. Bacteriol. 36: 228-240
8. Bric, J. M., M. B. Richard, and E. S. Sara. (1991). Rapid in situ assay for indole acetic acid production by bacteria immobilized on nitrocellulose membrane. Appl. Environ. Microbiol. 57: 535-538.
9. Chen W. and T. A. Kuo. (1993). A simple and rapid method for the preparation of gram negative bacterial genomic DNA. Nucleic Acids Res. 21: 2260.
10. Chopade, B. A., P. J. Wise and K. J. Towner. (1985). Plasmid transfer and behavior in *Acinetobacter calcoaceticus* EBF65/65. J. Gen. Microbiol. 131: 2805-2811.
11. Chopade, B. A., R. B. Patwardhan, V. C. Vaidya, and S. Khaimar. (1994 a). Elimination of antibiotic and metal resistant plasmids in human pathogenic *Acinetobacter* species. In: Tropical Diseases: Molecular Biology and Control Strategies. Eds: S. Kumar; A. K. Sen; G. P. Dutta and R. N. Sharma, CSIR Publications and Information Directorate, New Delhi, 695-703.
12. Chopade, B. A., R. B. Patwardhan, and P. K. Dhakephalkar. (1994 b). *Acinetobacter* infections in India: Genetic and molecular studies and some approaches to the problem. In: Tropical Diseases: Molecular Biology and Control Strategies. Eds: S. Kumar; A. K. Sen; G. P. Dutta and R. N. Sharma, CSIR Publications and Information Directorate, New Delhi, 704-717.
13. Clark, E., S. Manulis, Y. Ophir, I. Barash, and Y. Gafni. (1993). Cloning and characterization of iaaM and iaah from *Erwinia herbicola* pathovar gypsophilae. Phytopathol. 83:234-240.
14. Comai, L and T. Kosuge. (1982). Cloning and characterization of iaaM, a virulence determinant of *Pseudomonas savastanoi*. J. Bacteriol., 143: 950-957.
15. Costacurta, A and J. Vanderleyden. (1995). Synthesis of phytoharmones by plant associated bacteria. Crit. Riv. Microbiol. 21:1-18.
16. Deshpande, L. M., B. P. Kapadnis, and B. A. Chopade. (1993). Metal resistance in *Acinetobacter* and its relation to β-lactamase production. BioMetals. 6: 55-59.
17. Deshpande, L. M. and B. A. Chopade. (1994). Plasmid mediated silver resistance in *Acinetobacter baumannii* BioMetals, 7: 49-56.
18. Dhakephalker, P. K. and B. A. Chopade. (1994). High levels of multiple metal resistance and its correlation to antibiotic resistance in environmental isolates of *Acinetobacter* BioMetals. 7: 67-74.
19. Gerhardt, P., R. G. E. Murry, A. W. Wood., and N. R. Krieg. (1994). Methods in General and Molecular Bacteriology, American Society for Microbiology. Washington, D.C, U.S.A., 140.
20. Gordon, S. A., and Weber, R. P. (1951). Colorimetric estimation of indoleacetic acid. Plant Physiol., 26: 192-195.
21. Henriksen S. D. (1973). *Moraxella, Acinetobacter*, and *Mimeae*. Bacteriol. Rev., 37: 522-561.
22. Holtons, J. (1983). A note on preparation and use of a selective differential medium for the isolation of *Acinetobacter* spp. from clinical sources. J. Appl. Microbiol., 54: 141-142.
23. Huddedar S. B. and B. A. Chopade. (2000). Studies on distribution, and characterization of *Acinetobacter* spp. isolated from rhizosphere of wheat exhibiting antifungal and antibacterial activity. http://www.microbiologyou.com. In proceedings of: International Conference on Microbial Biotechnology Public Policy and Trade (ICMBT), Osmania University, Hyderabad., Paper No. 13.1-16.
24. John G. H, R. K. Noel, H. A S. Peter, T. S. James and T. W. Stanley. (1994). Bergey's Manual of Determinative Bacteriology, Williams & Wilkins, Baltimore, Md., USA. 73, 129.
25. Juni, E. (1972). Interspecies transformation of *Acinetobacter*: genetic evidence for a ubiquitous genus. J. Bacteriol., 112: 917-931.
26. Juni, E. (1978), Genetics and Physiology of *Acinetobacter*. Ann. Rev. Microbiol. 32: 349-371.
27. Kado, C. I. and S T. Liu. (1981). Rapid procedure for detection and isolation of large and small plasmids. J. Bacteriol., 145:1365-1375.
28. Kleeberger, A., H. Castorph, and W. Klingmuller. (1983). A comparative study on gram negative bacteria isolated from rhizosphere of wheat. Arch Microbiol., 136: 306-311.
29. Koga, J., T. Adachi, and H. Hidaka. (1991). IAA biosynthetic pathway from tryptophan via indole 3 pyruvic acid in *Enterobacter cloacae*. Agric. Biol. Chem., 55: 701-706.
30. Kulkarni, M. B., S. B. Gatpande and S. D. Gore. (1999). Common Statistical Tests. Satyajeet Prakashan, Pune, India. 105-112.
31. Leinhos, V and O. Vocek. (1984). Biosynthesis of auxins by phosphate solubilizing rhizobacteria from wheat and rye. Microbiol. Res. 149(1): 31-35.
32. Lippmann, B., V. Leinhos, and H. Bergmann. (1995). Influence of auxin producing rhizosbacteria on morphology and nutrient accumulation of crops. I. changes in root morphology and nutrient accumulation in maize (Zea maize L) caused by inoculation with indole-3-acetic acid (IAA) producing *Pseudomonas* and *Acinetobacter* strains or IAA applied exogeneously. Angew. Bot. 69(1/2): 31-36.
33. Naik, G. A., L. N. Bhat, B. A. Chopade and J. M. Lynch. (1994). Transfer of broad-host-range antibiotic resistance plasmids in soil microcosoms. Curr. Microbiol. 28: 209-215.
34. Patil, J. R. and B. A. Chopade. (2001). Studies on bioemulsifier production by *Acinetobacter* strains isolated from healthy human skin. J. Appl. Microbiol. 91: 290-298.
35. Subba Rao, N. S. (1986). The Rhizosphere, Chapt. 4, Interactions between Plant and Microorganisms., $2^{nd}$ ed. Wiley & Willsons, Oxford and IBH Publication Co. New Delhi, India, 50-80.
36. Subba Rao, N. S. (1988). Biofertilizers in Agriculture, In Interactions between plant and microorganisms. $3^{rd}$ ed. Wiley & Willsons, Oxford and IBH Publication Co. New Delhi, India. 1-188.
37. Saha, S. C. and B. A. Chopade, (2001). Studies on occurrence and distribution of *Acinetobacter* spp. and other gram negative bacteria from meat. J. Food. Sci. Technol. 38(1): 17-22.
38. Sambrook, J, E. F. Fritsch, and T. Maniatis, (1989). Molecular Cloning, A Laboratory Mannual, $2^{nd}$ edition, CSH Publication, Vol. 1, Cold Spring Harbor Laboratory press, New York, USA.
39. Shakibaie, M. R., P. K. Dhakephalkar, B. P. Kapadnis and B. A. Chopade. (1999). Removal of silver from photographic waste water effluent using *Acinetobacter baumannii* BL54. Can. J. Microbiol. 45: 995-1000.
40. Towner, K. J. and B. A. Chopade. (1986). Biotyping of *Acinetobacter calcoaceticus* using API 20 NE system. J. Hosp. Infect. 10: 145-151.

The invention claimed is:

1. The plasmid pUPI126.

2. A *Acinetobacter* strain comprising the plasmid pUPI126.

3. The *Acinetobacter* strain of claim 2, wherein the strain is *Acinetobacter haemolyticus* strain MTCC 5218.

4. A bioinoculum for wheat plant, said bioinoculum comprising one or more *Acinetobacter* strains according to claim 2; and a carrier.

5. A bioinoculum as claimed in claim 4 wherein the carrier is lignite.

6. A method of promoting wheat plant growth, said method comprising treating wheat seeds with the bioinoculum according to claim 4.

7. The method as claimed in claim 6, wherein the bioinoculum comprises the *Acinetobacter haemolyticus* strain MTCC 5218.

8. The method as claimed in claim 4 wherein the carrier in the bioinoculum is lignite.

9. The method as claimed in claim 4 wherein the *Acinetobacter* strain colonizes the wheat seeds during treatment.

10. The method as claimed in claim 4 wherein the color of the leaf of the wheat plant becomes darker green.

11. The method as claimed in claim 4 wherein the inflorescence and fruiting stages of the wheat plant is reached in a time duration lessened by 10 days.

* * * * *